United States Patent [19]

Heissenberger

[11] 4,099,614

[45] Jul. 11, 1978

[54] PACKAGE FOR A STERILIZED PAIR OF GLOVES AND METHOD OF FORMING THE SAME

[75] Inventor: Oswald Heissenberger, Pottschach, Austria

[73] Assignee: Semperit Aktiengesellschaft, Vienna, Austria

[21] Appl. No.: 754,088

[22] Filed: Dec. 23, 1976

[30] Foreign Application Priority Data

Jul. 22, 1976 [CH] Switzerland ..................... 9435/76

[51] Int. Cl.² ............................................. B65D 85/18
[52] U.S. Cl. ................................ 206/299; 53/21 FW; 53/32; 206/438; 229/87 A
[58] Field of Search ............. 53/21 FW, 32; 206/278, 206/292, 295, 297, 299, 438; 229/87 A

[56] References Cited

U.S. PATENT DOCUMENTS

| | | | |
|---|---|---|---|
| 3,187,987 | 6/1965 | Langdon | 206/299 X |
| 3,369,657 | 2/1968 | Quade et al. | 206/299 |
| 3,391,855 | 7/1968 | Ansell | 229/87 A X |
| 3,412,851 | 11/1968 | Coulombe | 206/299 |

*Primary Examiner*—Othell M. Simpson
*Assistant Examiner*—John Sipos
*Attorney, Agent, or Firm*—Werner W. Kleeman

[57] ABSTRACT

A package for a pair of sterilized gloves used for medical purposes and a method of forming such package, wherein the upper and lower ends of a sheet are folded at right angles to the lengthwise direction of the inserted gloves for covering the tips and the cuffs of such gloves. Then two lateral folds are formed substantially parallel to the lengthwise direction of the gloves at both sides of the same, there is then formed a fold at the central region of the sheet perpendicular to the lengthwise direction of the gloves, and then a fold centrally and parallel to the lengthwise direction of the gloves.

13 Claims, 3 Drawing Figures

PACKAGE FOR A STERILIZED PAIR OF GLOVES AND METHOD OF FORMING THE SAME

BACKGROUND OF THE INVENTION

The present invention relates to a new and improved package for articles, in particular sterilized pairs of gloves used for medical purposes, which package is formed from a sheet, for example paper, of essentially rectangular configuration which is folded parallel to all four sides and then centrally. This invention also relates to a method of forming such package.

When packaging sterilized pairs of gloves used for medical purposes different factors must be taken into account, namely: firstly, the package should be of a nature such that the packaging operation can be easily automated in order to prevent any contamination of the packaged product by handling. Secondly, the package should be configured such that when opening the same as large as possible area of the gloves, especially the fingers, remain covered up to the last moment prior to use. Thirdly, the gloves should be packaged in a manner that they can be removed from the package without any difficulty and placed upon the hands of the surgeon or the like without contacting the sterilized surfaces.

While taking into account these requirements there has become known to the art a glove package composed of an essentially rectangular sheet of paper which initially is folded over to both sides of the adjacently situated gloves of a pair parallel to the lengthwise direction of the gloves and then perpendicular to such lengthwise direction. In this way a pocket is formed in which the pair of gloves is located. This pocket is then again folded over centrally between the gloves, so that there is formed a package approximately of a size corresponding to a glove. This package is thereafter placed into a likewise sterilized bag, so that it then can be shipped. The drawback associated with this package and its fabrication is that upon opening the package initially the folds or folded portions must be opened from the top and the bottom and thereafter the folds to both sides of the gloves, with the result that the entire area of the gloves is immediately freely exposed and subjected to the effects of the atmosphere. In order to prevent contacting the gloves during opening of the lateral folds or folded portions, the latter are once again folded over outwardly a slight amount at their edges, so that the fingers of the person opening the package do not have to contact the gloves. This of course constituted an additional complicated operation in forming the package, resulting in increased costs owing to the required automatic operations. Furthermore, considered from the standpoint of the expenditure of material and also the cost thereof, what is disadvantageous with this prior art packaging technique and the package formed thereby, is also the size of the paper which is needed in order to package the pair of gloves. Since it is absolutely necessary to have the gloves covered up to the last moment prior to use, the lateral folds or folded portions are each folded over towards the center, with the result that the width of the paper must be at least twice as large as the space occupied by both of the adjacently situated gloves. Equally the material needed for forming the bags into which there are filled the gloves which have been folded into the paper package, is considerable since such likewise must correspond approximately to the size of a glove.

SUMMARY OF THE INVENTION

Therefore, with the foregoing in mind it is a general object of the present invention to provide an improved package for packaging sterilized pairs of gloves, and a method of forming the same, which is not associated with the aforementioned drawbacks and limitations of the prior art proposals.

Another and more specific object of the present invention aims at the provision of a new and improved construction of package of the previously mentioned type, and a method of forming the same, which protects and maintains covered the sensitive parts of the glove, namely, the fingers for as long as possible period of time, while nonetheless requiring a smaller amount of packaging material.

Now in order to implement these and still further objects of the invention, which will become more readily apparent as the description proceeds the package of the previously mentioned type is formed by carrying out the following sequence of operations:

(1) forming an upper fold and a lower fold substantially perpendicular to the lengthwise direction of the gloves for covering the fingers of the gloves and at least part of each cuff, which is preferably folded- or doubled-over;

(2) forming two lateral folds to both sides of the gloves substantially parallel to the lengthwise direction of the gloves;

(3) forming a fold centrally and perpendicular to the lengthwise direction of the gloves; and (4) forming a fold centrally and substantially parallel to the lengthwise direction of the gloves.

With this packaging technique as contemplated by the invention the pair of gloves, which as a general rule have the cuffs thereof folded-over up to about the region of the fingers, so that during opening of the package contamination of the outside of the gloves does not occur, is placed upon the paper. Then the paper is folded over from the top approximately to a point covering the fingers and then from the bottom approximately to the center of the folded-over cuffs. Thereafter, both of the lateral folds are formed to both sides of the gloves, extending essentially parallel to the lengthwise direction of the gloves. In this way there is formed a folded pocket in which there are fixed the gloves. This pocket is then folded at its center symmetrically and substantially perpendicular to the lengthwise direction of the gloves and therefore its size decreased by one-half, and thereafter again reduced in size to one-quarter of the original size of the pocket by forming a further central symmetrical fold. The thus folded package is then placed into a bag or sack which is closed and ready to be shipped.

During unpackaging of the gloves the package is first of all removed from the bag or sack and then initially unfolded to the original size of the pocket. Thereafter, the lateral folds are opened or bent-out and the gloves then can be removed. Until the actual time of removal of the gloves the fingers are covered and protected against contamination. During opening of the package of this development only very few and minor manipulations are needed, appreciably benefiting the safety and precision of the procedures which are being carried out in the operating room.

Furthermore, the paper requirements for the package of the invention are smaller than with heretofore known packages, since the inventive package utilizes the presence of the folded-over cuffs in such a manner that at this region there is not required any complete covering thereof. Also, with this manner of folding the paper according to the invention, it is possible, without any difficulty, to reduce the size of the package to one-quarter of the fold pocket, something which was not readily possible with heretofore known packages. Consequently, there is realized the benefit that also the bag, into which there is filled the package, can possess a smaller size.

Continuing, in order to additionally safeguard against possible contamination it is advantageous if the edge of the upper fold or folded portion is folded over approximately 0.5 to about 3 cm, preferably between about 1 to 2 cm. Thus, if necessary, also the paper can be completely opened without contacting the gloves, whereby the gloves are then freely exposed for removal.

In order to save paper or other sheet material used to form the package and yet provide the necessary safeguards against contamination, it is advantageous if the upper fold or folded portion extends approximately to the center of the package. In this way there is insured that in any case the fingers will be covered, whereas the lower portion of the gloves are protected, in any event, due to the folding- or doubling-over of the cuffs.

To prevent accidental dropping-out of the gloves during manipulation of the half opened package, it is further advantageous if the lower fold extends up to about one-sixth to about one-quarter of the package. In this way there can be obtained adequate fixation of the gloves without having to appreciably increase the amount of paper which is needed to form the package. The same considerations are applicable with respect to the lateral folds which advantageously likewise extend approximately over one-sixth to one-quarter of the package.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
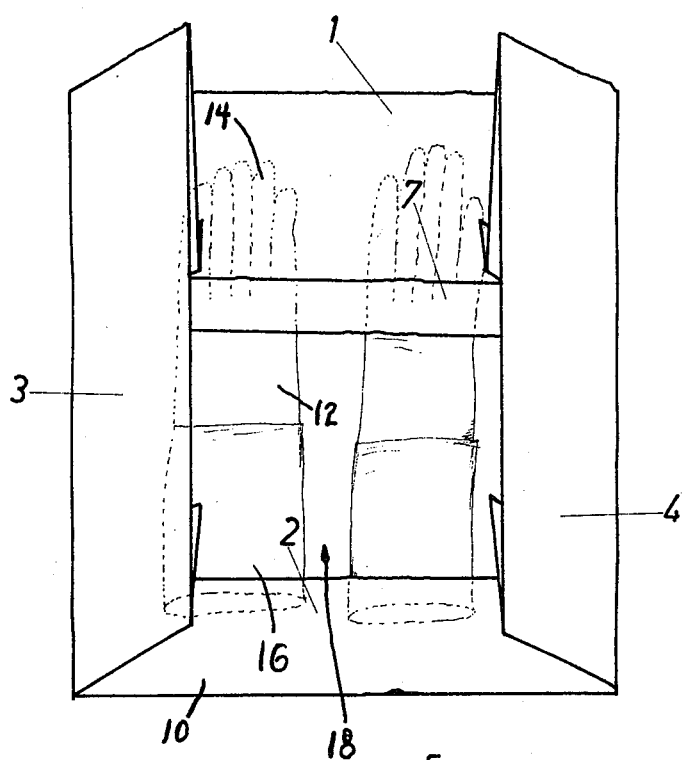
FIG. 1 is a plan view of a sheet of material, typically paper, during one stage of folding of the package of the invention.

Describing now the drawings, it will be seen by referring to FIG. 1 that a sheet of material 10, preferably formed of paper, but which could be formed of another suitable material, such as plastic, has placed on one side thereof, in adjacent relationship, a pair of gloves 12, each having fingers 14 and a cuff 16, which cuff is preferably folded-over. To form the package the gloves 12 are held in a fold or folded pocket 18, shown in FIG. 1, produced by forming an upper fold or folded portion 1, a lower fold or folded portion 2 and two lateral folds or folded portions 3 and 4. The upper fold 1 and the lower fold 2 are formed by folding over the upper and lower edges of the sheet 10 in a direction towards the fingers 14 and cuffs 16 respectively, of the gloves 12, and at essentially right angles to the lengthwise direction of such gloves. The upper fold 1 extends over the fingers 14 covering at least the proximal region thereof, to thereby protect the same against contamination, whereas the lower fold 2 covers at least the rear end of the cuffs 16. If the glove cuff is doubled-over, for instance as shown in the illustrated exemplary embodiment, the lower fold 2 need not extend as far over the cuff portion or rear end of the glove since the doubled-over cuff already protects the surface of the glove. The upper fold 1 may extend approximately to the center of the package, and can amount to about 0.5 to about 3 cm, preferably approximately 1 to 2 cm. The lower fold 2 and the lateral folds 3 and 4 can extend approximately between one-sixth to one-quarter of the package. The edge 7 of the upper fold or folded portion 1 will be seen, in the embodiment under discussion, to have been upwardly folded over once again a small amount. These folding operations can be carried out in a completely sterilized manner, without any difficulties, by automatic packaging machines.

Figure 2:
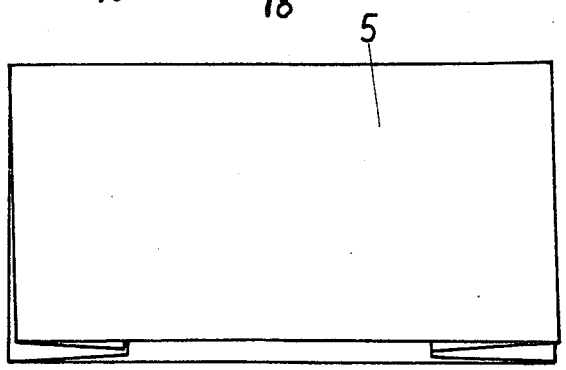
FIG. 2 illustrates a further step during folding of the package.
Figure 3:
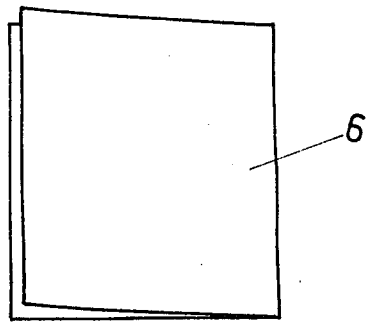
FIG. 3 illustrates a still further step during folding of the package.

In FIG. 2 there is shown the formulation of the central fold or folded portion 5 which reduces by one-half the size of the folded pocket 18, and in FIG. 3 the folded pocket is reduced in size further by a folding operation which reduces the folded pocket to one-quarter of its original size.

It will be recognized that by carrying out the aforementioned folding operations there is formed in a very simple and efficient manner a package 6 which protectively encloses the gloves 12 until ready to be used, and thereafter allows the package to be opened in an extremely simple manner without any great likelihood of contaminating the gloves or other packaged article.

While there are shown and described present preferred embodiments of the invention, it is to be distinctly understood that the invention is not limited thereto, but may be otherwise variously embodied and practiced within the scope of the following claims. ACCORDINGLY,

What I claim is:

1. A package for at least one pair of sterilized gloves used for medical purposes comprising an essentially rectangular sheet of material folded substantially parallel to all four sides and subsequently at a central region, the improvement comprising:
   an upper fold and a lower fold having edges spaced from one another, said folds being disposed essentially at right angles to the lengthwise direction of the gloves for completely covering, in contacting relation therewith, the fingers of the gloves and at least part of the cuffs of the gloves;
   two lateral, uncut folds to both sides of the pair of gloves essentially parallel to the lengthwise direction of the gloves and overlying said upper and lower folds;
   a further fold at the center between the edges of both said upper and lower folds and essentially at right angles to the lengthwise direction of the gloves, such that said gloves are folded at right angles to their lengthwise direction and only said lateral folds and said central region of said sheet of material are folded by said further fold; and
   a final fold centrally and essentially parallel to the lengthwise direction of the folded gloves such that only said upper and lower folds and said central region of said sheet of material are folded by said final fold to thereby form a compact glove package requiring a minimum amount of sheet material.

2. The package as defined in claim 1, wherein the edge of the upper fold is folded over approximately 0.5 to 3 cm.

3. The package as defined in claim 2, wherein the edge of the upper fold is folded over approximately 1 to 2 cm.

4. The package as defined in claim 1, wherein the upper fold is folded over approximately towards the center of the package.

5. The package as defined in claim 1, wherein the lower fold is folded over so as to extend a distance corresponding approximately between one-sixth to one-quarter of the package.

6. The package as defined in claim 1, wherein the lateral folds are folded over to extend a distance corresponding approximately one-sixth to one-quarter of the package.

7. A method of packaging at least one pair of sterilized gloves used for medical purposes comprising the steps of:

placing a pair of gloves along side one another upon a sheet of packaging material having a central region, upper and lower edges and uncut lateral edges;

first folding the upper edge and the lower edge of the sheet to thereby form an upper fold and a lower fold with said upper and lower edges spaced from one another and essentially at right angles to the lengthwise direction of the gloves for completely covering the fingers of the gloves and at least part of the cuffs of the gloves;

folding, after the first folding step, the lateral edges of the sheet to thereby form two lateral folds to both sides of the pair of gloves essentially parallel to the lengthwise direction of the gloves thereby enclosing the gloves in a pocket bounded by the upper and lower folds and the two lateral folds;

after forming the lateral folds, forming a first central fold at the center of the pocket between the upper and lower edges and essentially at right angles to the lengthwise direction of the gloves such that only said lateral folds and said central region of the sheet are folded by said first central fold; and after forming the first central fold, forming a second central fold at the thus folded pocket centrally and essentially parallel to the lengthwise direction of the gloves such that only said upper and lower folds and said central region of the sheet are folded by said second central fold to thereby form a compact glove package requiring a minimum amount of packaging material.

8. The method as defined in claim 7, including the step of folding the edge of the upper fold over approximately 0.5 to 3 cm.

9. The method as defined in claim 8, wherein the edge of the upper fold is folded over approximately 1 to 2 cm.

10. The method as defined in claim 7, including the step of folding the upper edge over approximately towards the center of the package.

11. The method as defined in claim 7, including the step of folding the lower fold over so as to extend a distance corresponding approximately between one-sixth to one-quarter of the package.

12. The method as defined in claim 7, wherein the lateral folds are folded over to extend a distance corresponding to approximately one-sixth to one-quarter of the package.

13. A glove package for at least one pair of sterilized gloves produced according to the method comprising the steps of:

placing a pair of gloves along side one another upon a sheet of packaging material having a central region, upper and lower edges and uncut lateral edges;

first folding the upper edge and the lower edge of the sheet to thereby form an upper fold and a lower fold with said upper and lower edges spaced from one another and essentially at right angles to the lengthwise direction of the gloves for completely covering the fingers of the gloves and at least part of the cuffs of the gloves;

folding, after the first folding step, the lateral edges of the sheet to thereby form two lateral folds to both sides of the pair of gloves essentially parallel to the lengthwise direction of the gloves thereby enclosing the gloves in a pocket bounded by the upper and lower folds and the two lateral folds;

after forming the lateral folds, forming a first central fold at the center of the pocket between the upper and lower edges and essentially at right angles to the lengthwise direction of the gloves such that only said lateral folds and said central region of the sheet are folded by said first central fold; and after forming the first central fold, forming a second central fold at the thus folded pocket centrally and essentially parallel to the lengthwise direction of the gloves such that only said upper and lower folds and said central region of the sheet are folded by said second central fold to thereby form a compact glove package requiring a minimum amount of packaging material.

* * * * *